(12) United States Patent
Cai et al.

(10) Patent No.: US 10,729,449 B2
(45) Date of Patent: Aug. 4, 2020

(54) FIRING COUNTER FOR MEDICAL DEVICES

(71) Applicant: Covidien LP, Mansfield, MA (US)

(72) Inventors: Longsheng Cai, Shanghai (CN);
Shunhong Xu, Shanghai (CN); Lin Chen, Shanghai (CN)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 15/769,805

(22) PCT Filed: Nov. 16, 2015

(86) PCT No.: PCT/CN2015/094655
§ 371 (c)(1),
(2) Date: Apr. 20, 2018

(87) PCT Pub. No.: WO2017/084000
PCT Pub. Date: May 26, 2017

(65) Prior Publication Data
US 2020/0146684 A1    May 14, 2020

(51) Int. Cl.
*A61B 17/128* (2006.01)
*A61B 90/00* (2016.01)
*A61B 17/00* (2006.01)

(52) U.S. Cl.
CPC .......... *A61B 17/1285* (2013.01); *A61B 90/08* (2016.02); *A61B 2017/00407* (2013.01); *A61B 2090/0803* (2016.02)

(58) Field of Classification Search
CPC . A61B 17/068; A61B 17/128; A61B 17/1285; A61B 2090/0803
See application file for complete search history.

(56) References Cited

U.S. PATENT DOCUMENTS

| | | |
|---|---|---|
| 4,712,549 A | 12/1987 | Peters et al. |
| 8,430,892 B2 | 4/2013 | Bindra et al. |
| 9,186,136 B2 | 11/2015 | Malkowski et al. |
| 9,364,216 B2 | 6/2016 | Rockrohr et al. |
| 9,364,240 B2 | 6/2016 | Whitfield et al. |
| 2013/0131697 A1 | 5/2013 | Hartoumbekis |
| 2017/0027570 A1 | 2/2017 | Murthy Aravalli |
| 2017/0027575 A1 | 2/2017 | Murthy Aravalli |

*Primary Examiner* — Melanie R Tyson
(74) *Attorney, Agent, or Firm* — Carter, DeLuca & Farrell LLP (57) ABSTRACT

A surgical device includes a handle assembly and a firing counter assembly. The handle assembly includes a housing defining a window, a trigger, and a drive member axially movable within the housing and operatively coupled with the trigger. The firing counter assembly includes a camming pin and a sleeve rotatably supported about the drive member and defining a continuous groove. The sleeve has indicia circumferentially arranged about the sleeve and corresponding to the number of surgical clips in the surgical device. The camming pin is supported on the drive member for concomitant axial displacement with the drive member. The camming pin is configured to slide through the continuous groove of the sleeve, wherein actuation of the trigger causes rotation of the sleeve such that the indicia corresponding to the number of surgical clips remaining in the surgical device is shown through the window of the housing.

22 Claims, 10 Drawing Sheets

FIRING COUNTER FOR MEDICAL DEVICES

CROSS-REFERENCE TO RELATED APPLICATIONS

This application is a U.S. National Stage Application filed under 35 U.S.C. § 371(a) which claims the benefit of and priority to International Patent Application Serial No. PCT/CN2015/094655, filed Nov. 16, 2015, the entire disclosure of which is incorporated by reference herein.

BACKGROUND

Technical Field

The present disclosure relates to surgical instruments and, more particularly, to endoscopic surgical clip appliers having a firing counter.

Description of Related Art

Surgical procedures frequently require the temporary or permanent occlusion of vessels to prevent the leakage of fluids, e.g., blood, through incisions made at the surgical site. A broad range of surgical ligating instruments and techniques exist for occluding vessels. These instruments generally provide a series of clips that are stored in the instrument and fed sequentially to the jaw mechanism at a distal end of the instrument upon actuation of a trigger at a proximal end of the instrument. As the trigger is actuated, the jaws close to form a clip positioned between the jaw members, and as the jaws are opened to release the formed clip, a new clip is fed from the series to a position between the jaws. This process may be repeated until all the clips in the series of clips have been used.

Accordingly, a need exists for a firing counter to keep track of the number of clips remaining in the instrument, while providing simple and cost effective integration of the firing counter with the instrument without diminishing functionality of the instrument.

SUMMARY

The present disclosure describes a surgical clip applier that demonstrates a practical approach to meeting the performance requirements and overcoming the usability challenges associated with a plurality of surgical clips that are stored in the surgical clip applier and fed sequentially to the jaw mechanism.

In accordance with an embodiment of the present disclosure, there is provided a surgical device including a handle assembly and a firing counter assembly. The handle assembly includes a housing defining a window, a trigger, and a drive member axially movable within the housing and operatively coupled with the trigger. The firing counter assembly includes a camming pin and a sleeve rotatably supported about the drive member and defining a continuous groove. The sleeve has indicia circumferentially arranged about the sleeve and corresponding to the number of surgical clips in the surgical device. The camming pin is supported on the drive member for concomitant axial displacement with the drive member. The camming pin is configured to slide through the continuous groove of the sleeve, wherein actuation of the trigger causes rotation of the sleeve such that the indicia corresponding to the number of surgical clips remaining in the surgical device is shown through the window of the housing.

In an embodiment, the continuous groove may include a plurality of proximal portions, a plurality of transition portions, and a first distal portion. Axial movement of the drive member from a proximal-most position to a distal-most position may cause the camming pin to slide from a first proximal portion of the plurality of proximal portions of the continuous groove to the first distal portion through a first transition portion of the plurality of transition portions of the continuous groove. In addition, axial movement of the drive member from the distal-most position to the proximal-most position may cause the camming pin to slide from the first distal portion of the continuous groove to a second proximal portion of the plurality of proximal portions of the continuous groove through a second transition portion of the plurality of transition portions of the continuous groove. The first distal portion may be disposed distal of the second proximal portion. In an embodiment, movement of the camming pin through the first or second transition portion of the plurality of transition portions of the continuous groove may rotate the sleeve.

In an embodiment, a pair of the plurality of transition portions of the continuous groove may define a bifurcated fork with the first distal portion of the continuous groove. In particular, a proximal end of the first distal portion of the continuous groove may be aligned with one of the pair of the plurality of transition portions of the continuous groove. In another embodiment, a pair of the plurality of transition portions may define a bifurcated fork with one of the plurality of proximal portions.

In an embodiment, the sleeve may define a passage configured to receive the drive member. The passage may define a central axis. The sleeve may be rotatable about the central axis.

In an embodiment, the plurality of proximal portions of the continuous groove may be substantially parallel to each other. Alternatively, the plurality of proximal portions of the continuous groove may be substantially parallel to the central axis. In another embodiment, the first distal portion of the continuous groove may be substantially parallel to the central axis of the sleeve.

In another embodiment, the plurality of proximal portions of the continuous groove may be uniformly arranged about the central axis.

In another embodiment, each of the plurality of transition portions of the continuous groove may define an acute angle with respect to the plurality of proximal portions of the continuous groove.

In another embodiment, the continuous groove may further include a second distal portion. In particular, the second distal portion may have a length shorter than a length of the first distal portion. The second distal portion may be dimensioned to inhibit return of the drive member to a proximal-most position.

In accordance with another embodiment of the present disclosure, there is provided a surgical clip applier including a handle assembly, an elongate member, a clip cartridge assembly, and a firing counter assembly. The handle assembly includes a housing defining a window, a trigger extending from the housing, and a drive assembly including a drive member axially movable within the housing and operatively coupled with the trigger. The elongate member extends distally from the handle assembly. The clip cartridge assembly is selectively loadable in the elongate member. The clip cartridge assembly has a number of surgical clips. The firing counter assembly includes a sleeve and a camming pin. In particular, the sleeve is rotatably supported about the drive member. The sleeve includes a number of indicia corresponding to the number of surgical clips in the clip cartridge assembly. The sleeve defines a camming groove. A camming pin is supported on the drive member. The camming pin is configured to slide through the camming groove of the sleeve, wherein actuation of the trigger causes rotation of the sleeve such that the indicia corresponding to the number of surgical clips remaining in the clip cartridge assembly is shown through the window of the housing.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figures 1, 2:
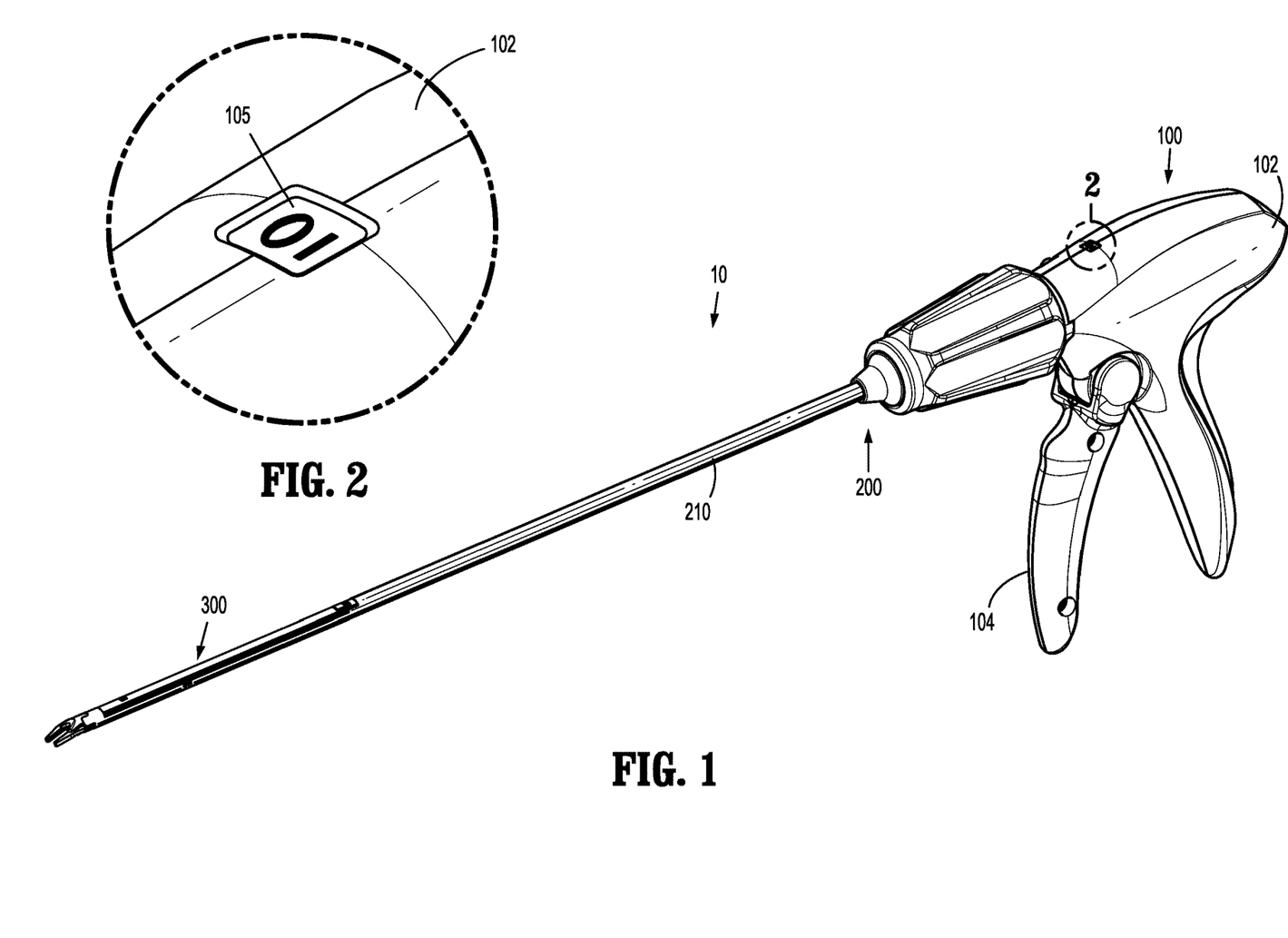
FIG. 1 is a perspective view of a surgical clip applier in accordance with an embodiment of the present disclosure.
FIG. 2 is an enlarged view of the indicated area of detail of FIG. 1.

Referring now to FIG. 1, an endoscopic surgical clip applier in accordance with an embodiment of the present disclosure is generally designated as 10. Surgical clip applier 10 forms multiple clips during a single insertion into a body cavity and generally includes a handle assembly 100, an endoscopic assembly 200, and a clip cartridge assembly 300. Handle assembly 100 includes a trigger 104. Endoscopic assembly 200 includes an elongate shaft 210 that is selectively connectable to handle assembly 100. Elongate shaft 210 may have various lengths tailored to meet the needs of the surgical procedure. Clip cartridge assembly 300 is configured to be selectively loaded into elongate shaft 210 of endoscopic assembly 200 and is actuated by trigger 104 of handle assembly 100 to fire and form surgical clips "C" (FIG. 11) onto underlying tissue and/or vessels.

With reference to FIGS. 1 and 2, handle assembly 100 includes a housing 102 having a window 105 to display a number corresponding to the number of surgical clips "C" (FIG. 11) remaining in clip cartridge assembly 300. Housing 102 of handle assembly 100 may be formed of a suitable plastic or thermoplastic material for sterilization. Alternatively, housing 102 may be fabricated from stainless steel of the like.

Figure 3:
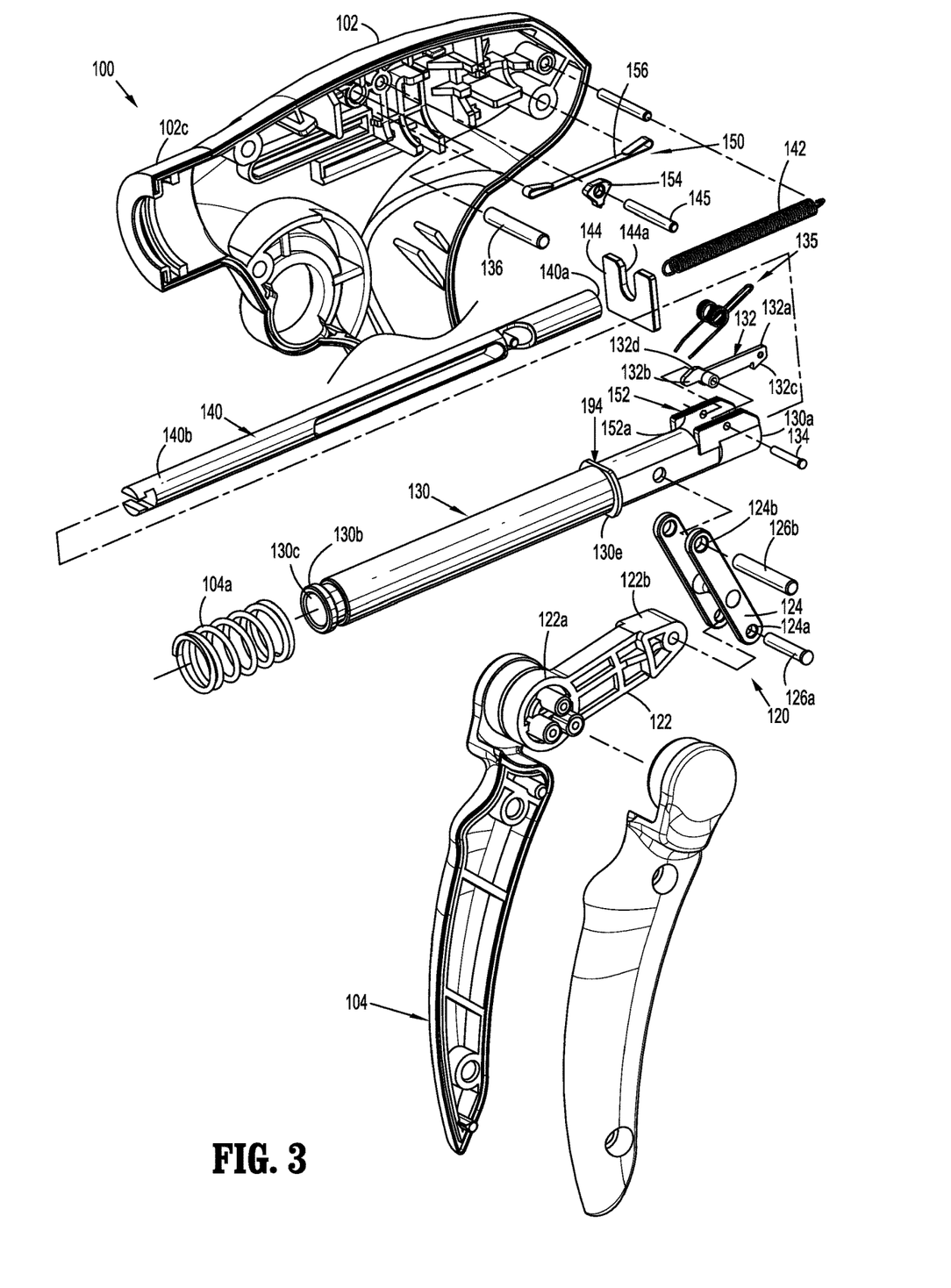
FIG. 3 is an exploded perspective view of the handle assembly of FIG. 1 illustrating the handle assembly with a firing counter assembly removed.
Figure 4:
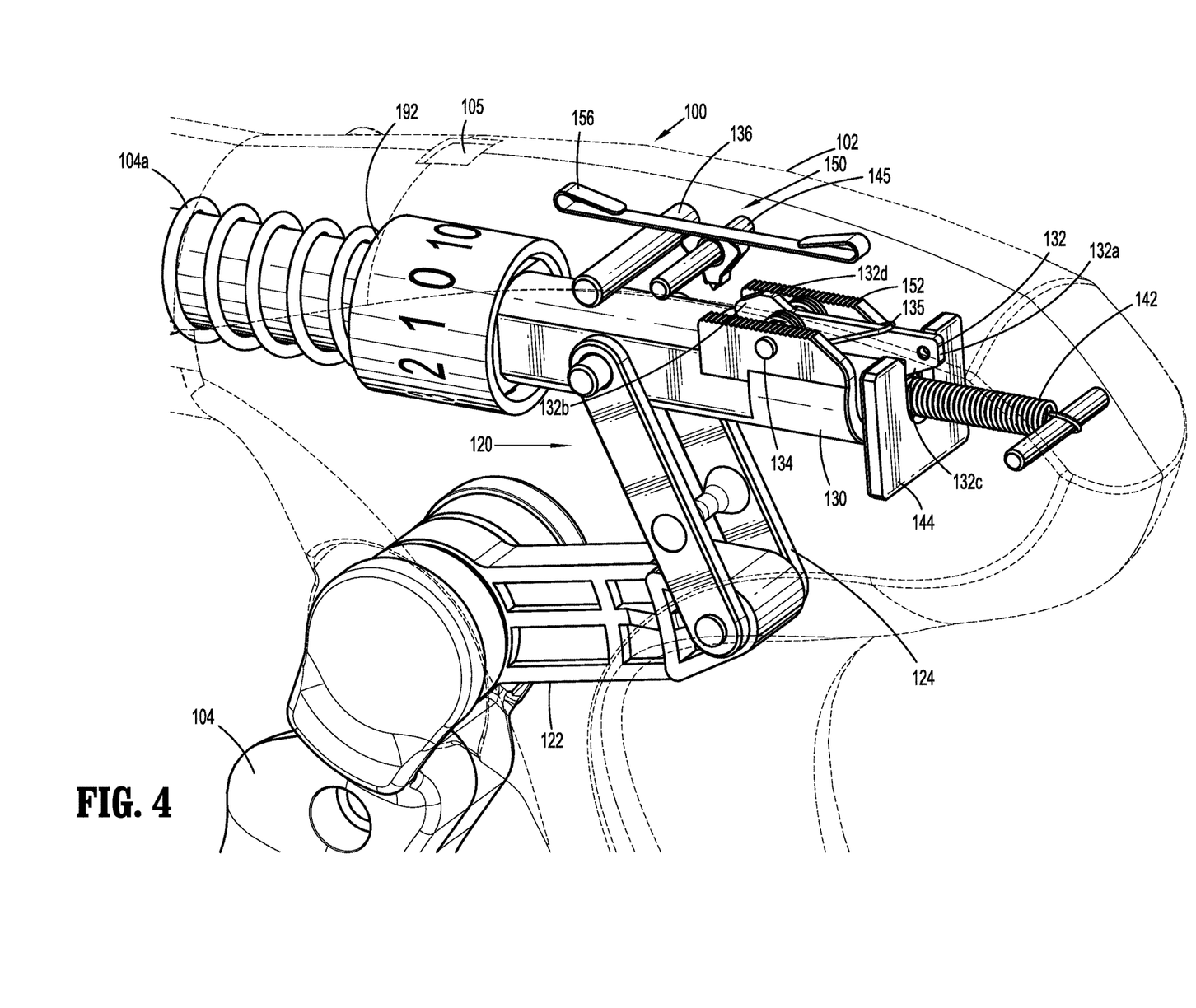
FIG. 4 is a perspective view of a drive assembly of the handle assembly of FIG. 1.

With reference now to FIGS. 3 and 4, handle assembly 100 includes a drive assembly 120 operatively connected to trigger 104. Drive assembly 120 includes a jaw pusher tube 130, a distal link arm 122 extending from trigger 104, and a proximal link arm 124 interconnecting distal link arm 122 and jaw pusher tube 130. Jaw pusher tube 130 is operatively coupled with jaw member 214 (FIG. 10) to approximate jaw member 214 and form the distal-most surgical clip "$C_1$" (FIG. 11) that is loaded therein, as will be discussed hereinbelow. Distal link arm 122 includes a distal coupling portion 122a which may be, e.g., keyed, to trigger 104 for concomitant pivoting upon actuation of trigger 104. A proximal coupling portion 122b of distal link arm 122 is pivotally connected to a proximal coupling portion 124a of proximal link arm 124. A distal coupling portion 124b of proximal link arm 124 is pivotally connected to jaw pusher tube 130. Distal link arm 122 and proximal link arm 124 are pivotally coupled by a first pin 126a. Distal coupling portion 124b of proximal link arm 124 is pivotally coupled to jaw pusher tube 130 by a second pin 126b. Under such a configuration, actuation of trigger 104 causes axial displacement of jaw pusher tube 130.

With continued reference to FIGS. 3 and 4, jaw pusher tube 130 is slidably supported within housing 102 of handle assembly 100 and defines a longitudinally extending passageway or lumen 130c configured to receive clip pusher bar 140 (FIG. 3) therein. Distal end 130b of jaw pusher tube 130 projects distally from nose 102c (FIG. 3) of housing 102. Drive assembly 120 further includes a biasing member 104a that is supported between an inner wall of nose 102c of housing 102 and flange 130e of jaw pusher tube 130 to bias jaw pusher tube 130 toward a proximal position. Movement of jaw pusher tube 130 towards a proximal position biases trigger 104 toward an unactuated condition. Biasing member 104a may be securely affixed to flange 130e projecting from jaw pusher tube 130.

Figure 5:
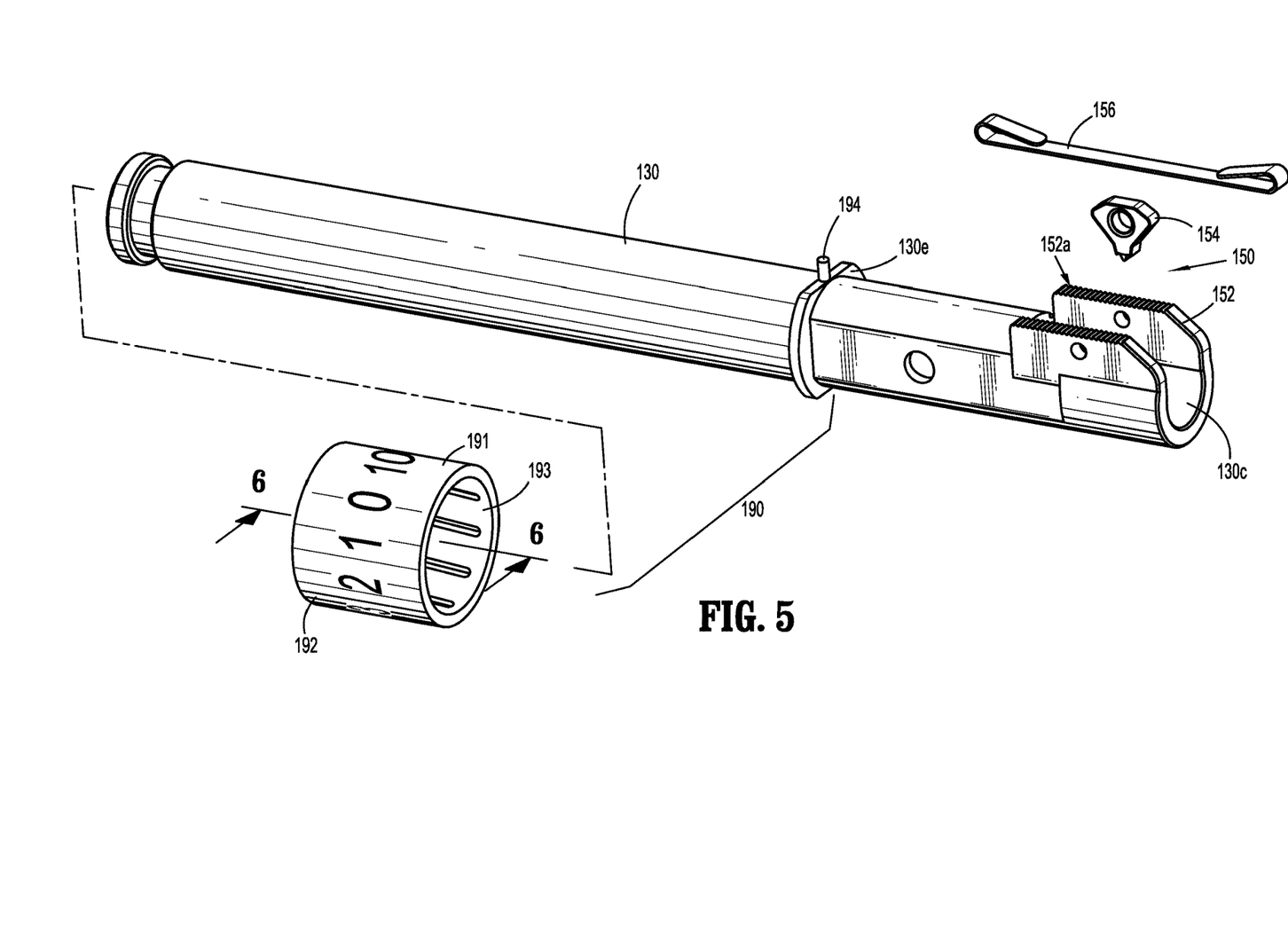
FIG. 5 is an exploded perspective view of a firing counter assembly of FIG. 4 for use with the handle assembly of FIG. 1.

With reference also to FIG. 5, at least one linear rack 152 including teeth 152a is disposed on jaw pusher tube 130. A release lever 132 is pivotally coupled to linear rack 152 by a pivot pin 134 (FIG. 3). Release lever 132 includes a proximal end 132a that extends proximal of proximal end 130a of jaw pusher tube 130. Proximal end 132a of release lever 132 includes a tooth 132c (FIG. 3) dimensioned to extend at least partially into proximal end 130a and/or lumen 130c of jaw pusher tube 130. Release lever 132 includes a distal end 132b that is positioned distal of pivot pin 134. Distal end 132b of release lever 132 includes a nub or ramp 132d projecting away from jaw pusher tube 130. A proximal end 132a of release lever 132 is biased toward lumen 130c (FIG. 5) of jaw pusher tube 130 by a biasing member 135. In embodiments, the biasing member 135 can include a leaf spring supported about pivot pin 134 and engaging an upper surface of release lever 132 proximally of pivot pin 134.

With particular reference to FIG. 4, drive assembly 120 further includes a camming pin 136 that is fixedly supported within housing 102 of handle assembly 100. Camming pin 136 is configured to pivot release lever 132 about pivot pin 134 when jaw pusher tube 130 is advanced distally through housing 102. More specifically, when ramp 132d of release lever 132 engages pin 136, ramp 132d is pushed toward jaw pusher tube 130. The bias of biasing member 135 is overcome and proximal end 132a of release lever 132 is pivoted upwardly away from jaw pusher tube 130.

With continued reference to FIGS. 3-5, clip pusher shaft 140 (FIG. 3) is slidably supported within lumen 130c of pusher tube 130. Clip pusher shaft 140 is operatively coupled with a clip pusher bar 218 (FIG. 10) of endoscopic assembly 200 and a cartridge clip pusher bar 304 (FIG. 11) of clip cartridge assembly 300 to load distal-most surgical clip "$C_1$" (FIG. 11) into jaw member 214. Clip pusher shaft 140 includes a proximal end 140a projecting proximally from proximal end 130a of jaw pusher tube 130, and a distal end 140b projecting distally from distal end 130b of pusher tube 130. Handle assembly 100 further includes a stop block 144 supported in housing 102. Stop block 144 is disposed proximal of clip pusher shaft 140 and defines a slot 144a configured to receive proximal end 132a of release lever 132 and biasing member 142 therethrough. Slot 144a is dimensioned such that at least a portion of proximal end 140a of clip pusher shaft 140 abuts against stop block 144 when clip pusher shaft 140 is in a proximal-most position.

Clip pusher shaft 140 is biased toward a proximal position by biasing member 142. Biasing member 142 may be, e.g., a tension spring. When jaw pusher tube 130 and clip pusher shaft 140 are located at respective proximal positions, tooth 132c of release lever 132 engages proximal end 140a of clip pusher shaft 140. Under such a configuration, when jaw pusher tube 130 is advanced distally, clip pusher shaft 140 is advanced with jaw pusher tube 130. However, when ramp 132d of release lever 132 engages pin 136 and is deflected toward jaw pusher tube 130, overcoming the bias of biasing member 135, proximal end 132a of release lever 132 moves away from jaw pusher tube 130 and tooth 132c of release lever 132 disengages from proximal end 140a of clip pusher shaft 140. At this time, biasing member 142 pulls clip pusher shaft 140 proximally into abutment with stop block 144.

With continued reference to FIGS. 3-5, handle assembly 100 further includes a ratchet assembly 150 supported within housing 102. Ratchet assembly 150 includes at least one linear rack 152 including teeth 152a. Ratchet assembly 150 further includes a ratchet pawl 154 pivotally connected to housing 102 by a pawl pin 145. Pawl 154 is biased toward rack 152 by a pawl spring 156 that maintains pawl 154 in engagement with teeth 152a of rack 152. Once pawl 154 engages rack 152, trigger 104 is inhibited from returning to a fully unactuated position until trigger 104 is fully actuated or until pawl 154 clears a proximal end of rack 152. When pawl 154 clears the proximal end of rack 152, pawl 154 reverses to allow advancement of pawl 154 back over rack 152 as the direction of movement of rack 152 changes between proximal and distal movement. This occurs when jaw pusher tube 130 reaches a proximal-most or distal-most position.

With particular reference to FIGS. 4 and 5, handle assembly 100 further includes a firing counter assembly 190 in accordance with an embodiment of the present disclosure. Firing counter assembly 190 includes a rotatable sleeve 192 and a camming pin 194. Rotatable sleeve 192 is rotatably supported about jaw pusher tube 130 and provides indicia corresponding to the number of surgical clips "C" remaining in surgical clip cartridge assembly 300 (FIG. 11) of clip applier 10. The indicia may be viewed through window 105 in housing 102 and includes numbers circumferentially arranged on an outer surface 191 of rotatable sleeve 192 such that each actuation of trigger 104 (or firing of surgical clip "C") results in predetermined rotation of rotatable sleeve 192 which, in turn, incrementally decreases the number shown through window 105.

Figure 6:
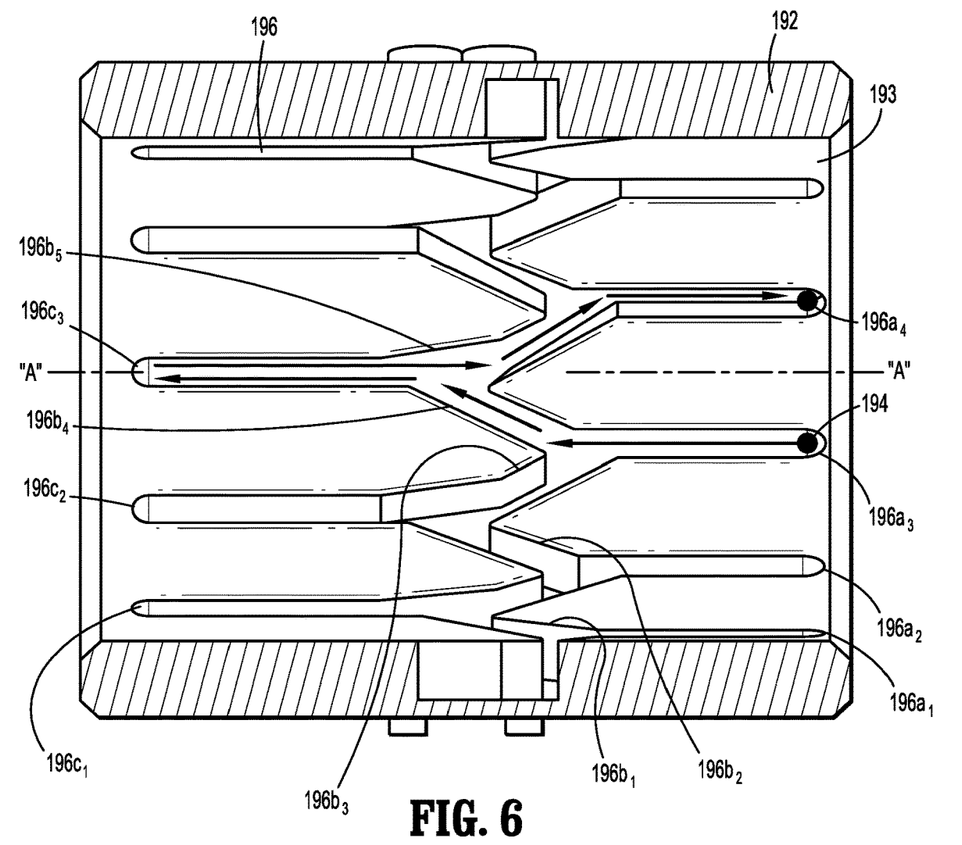
FIG. 6 is a side cross-sectional view of a sleeve of the firing counter assembly of FIG. 5 taken along section line 6-6 of FIG. 5.
Figure 7:
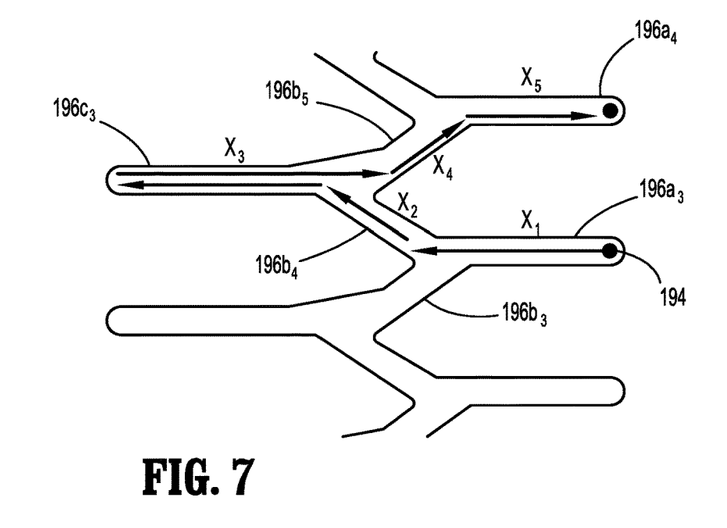
FIG. 7 is a schematic view of a partial travel path of a camming pin within the continuous groove of the sleeve of FIG. 6.

With reference now to FIGS. 6 and 7, rotatable sleeve 192 includes an inner surface 193 defining a continuous groove 196 that is configured to slidably receive camming pin 194 therethrough. Camming pin 194 extends radially outward from flange 130e (FIG. 5) of jaw pusher tube 130. As camming pin 194 slides through continuous groove 196, rotatable sleeve 192 is rotated by a predetermined amount, as described in detail below.

Continuous groove 196 includes a plurality of proximal portions $196a_{1\ldots n}$, a plurality of transition portions $196b_{1\ldots n}$, and a plurality of distal portions $196c_{1\ldots n}$. The plurality of proximal portions $196a_{1\ldots n}$ are substantially parallel to each other and to a longitudinal axis "A" defined by rotatable sleeve 192. The total number of proximal portions $196a_{1\ldots n}$ represents the total number of surgical clips "C" in clip cartridge assembly 300. For example, a clip cartridge assembly carrying 10 surgical clips would include 10 proximal portions $196a_{1\ldots n}$ uniformly arranged about rotatable sleeve 192. The plurality of distal portions $196c_{1\ldots n}$ are substantially parallel to each other and to longitudinal axis "A". Each transition portion $196b_{1\ldots n}$ interconnects a proximal portion $196a_{1\ldots n}$ with a corresponding distal portion $196c_{1\ldots n}$.

With particular reference to FIG. 7, a pair of adjacent transition portions $196b_{3,4}$ defines a bifurcated fork or Y-shape with an adjacent proximal portion $196a_3$, and a pair of adjacent transition portions $196b_{4,5}$ defines a bifurcated fork or Y-shape with an adjacent distal portion $196c_3$. However, proximal portion $196a_3$ is aligned with transition portion $196b_4$, and distal portion $196c_3$ is aligned with transition portion $196b_5$ such that camming pin 194 slides through a predetermined path. Each transition portion $196b_{4,5}$ defines an acute angle with respect to proximal and distal portions $196a_{3,4}$, $196c_3$. Upon actuation of trigger 104, camming pin 194 travels through continuous groove 196 in the direction of arrows $x_{1-5}$ in sequence.

Figure 8:
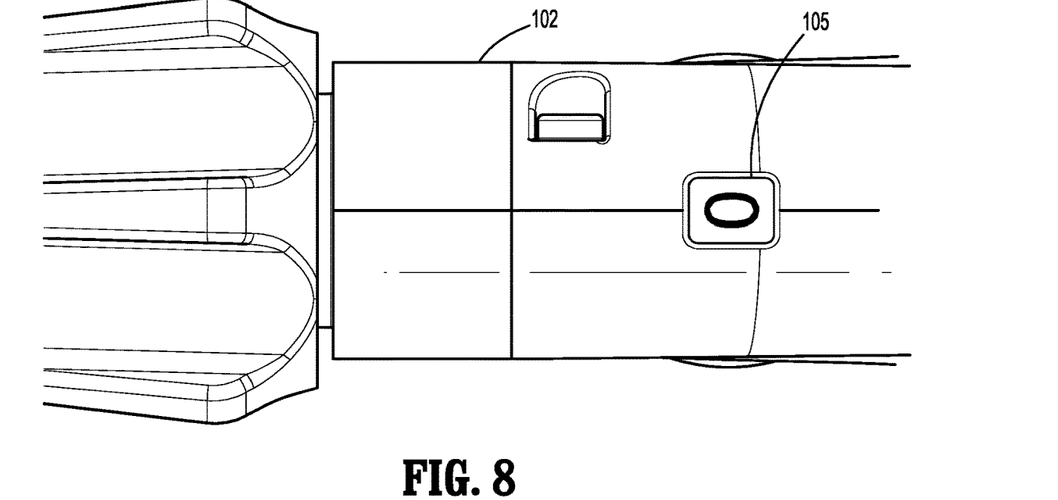
FIG. 8 is a partial top view of the handle assembly of FIG. 1 illustrating a window showing indicia corresponding to an empty clip cartridge assembly.
Figure 9:
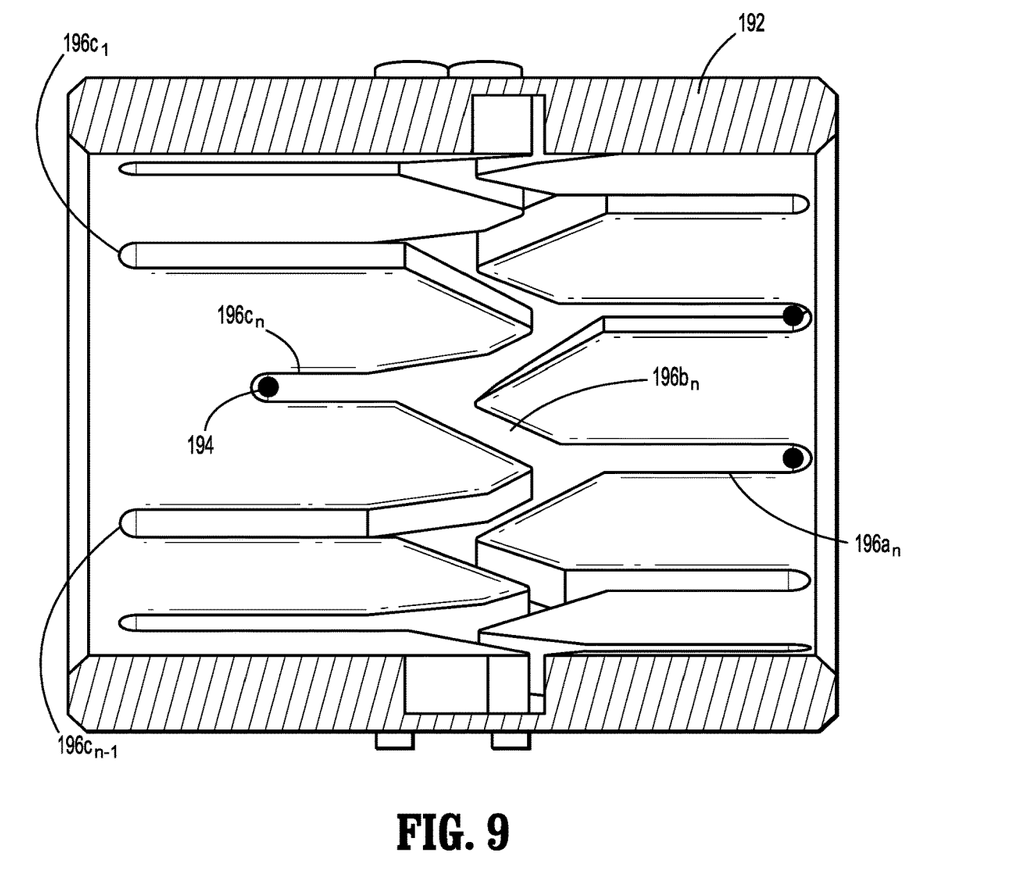
FIG. 9 is a cross-sectional view of the sleeve of FIG. 5 illustrating a lockout condition.
Figure 13:
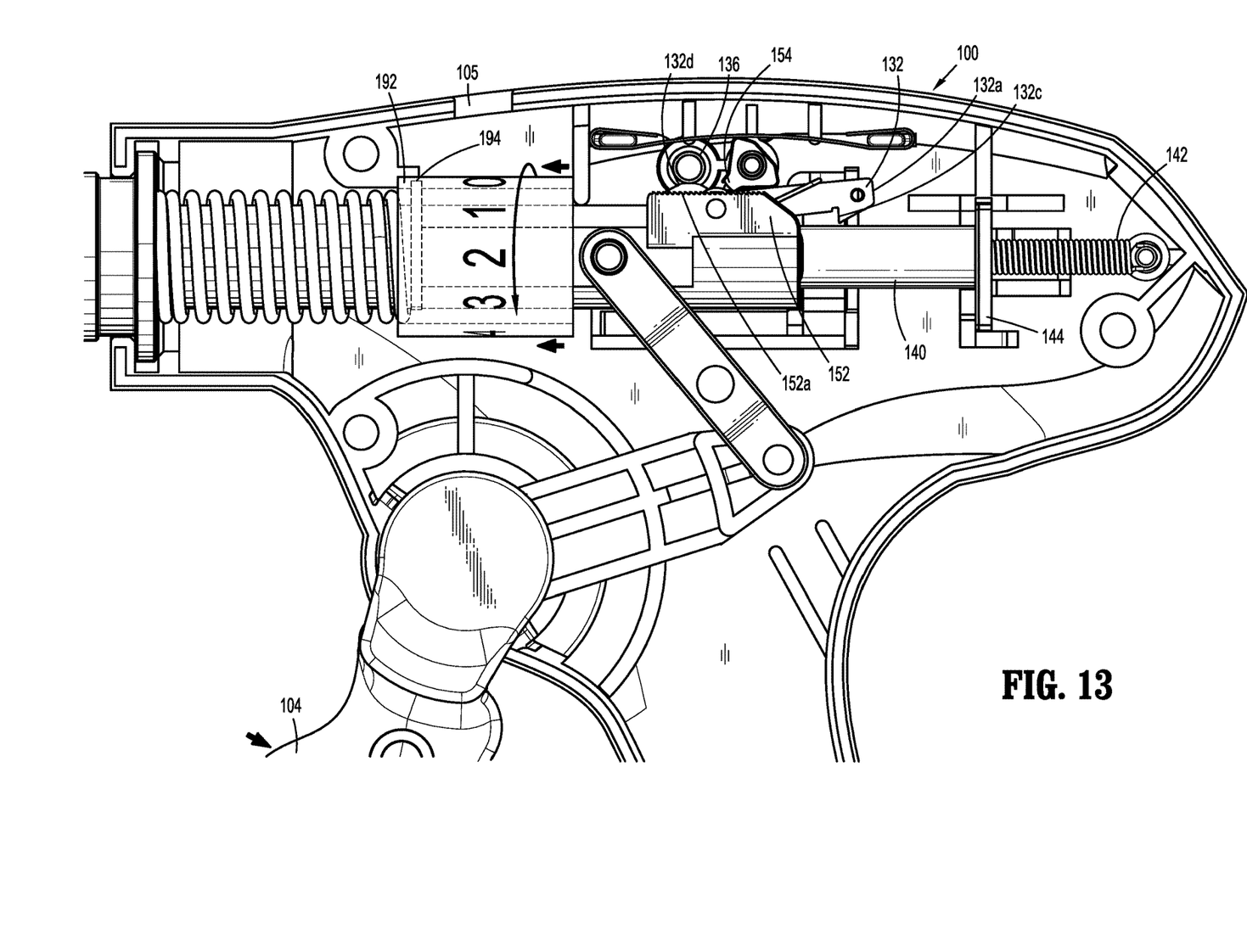
FIG. 13 is a side cross-sectional view of the handle assembly of FIG. 12 illustrating the handle assembly in an actuated condition.

With reference now to FIGS. 8 and 9, when last surgical clip "C" is fired, camming pin 194 travels from proximal portion $196a_n$ to distal portion $196c_n$ through transition portion $196b_n$. Distal portion $196c_n$ has a shorter length than those of other distal portions $196c_{1\ldots n-1}$. Under such a configuration, trigger 104 is unable to complete its stroke and pawl 154 of ratchet assembly 150 that is engaged with teeth 152a on rack 152 inhibits proximal movement or resetting of jaw pusher tube 130 (FIG. 13).

Figure 10:
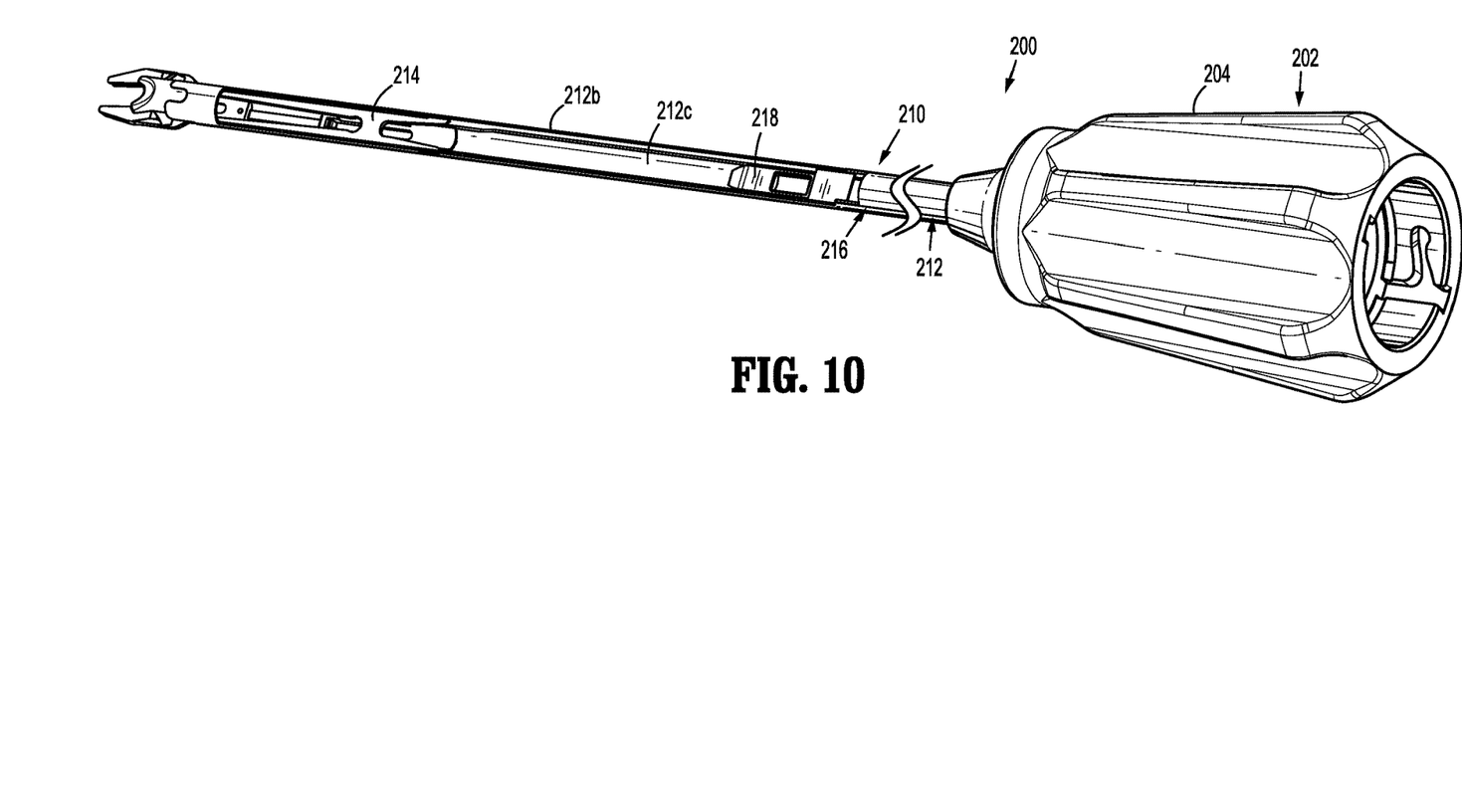
FIG. 10 is a perspective view of an endoscopic assembly of the surgical clip applier of FIG. 1.

With reference to FIG. 10, endoscopic assembly 200 of surgical clip applier 10 is shown. Endoscopic assembly 200 includes a knob assembly 202 configured for selective connection to handle assembly 100. Endoscopic assembly 200 includes an elongate shaft 210 extending from knob assembly 202. Elongate shaft 210 includes an outer tube 212, a jaw member 214 mounted in channel 212c of outer tube 212, and a jaw closure bar 216 slidably supported within outer tube 212. Jaw member 214 defines a channel therebetween for receipt of a surgical clip "C" therein. Jaw closure bar 216 is operatively coupled with jaw member 214 to actuate jaw member 214 to a closed position and form the distal-most surgical clip "$C_1$" that is loaded therein.

Elongate shaft 210 further includes a clip pusher bar 218 slidably supported within jaw closure bar 216. Clip pusher bar 218 is operatively coupled with a cartridge clip pusher bar 304 (FIG. 11) of clip cartridge assembly 300. Clip pusher bar 218 is operatively coupled with clip pusher bar 140 of drive assembly 120. Axial translation of clip pusher shaft 140 imparts axial translation on clip pusher bar 218 of endoscopic assembly 200.

Figure 11:
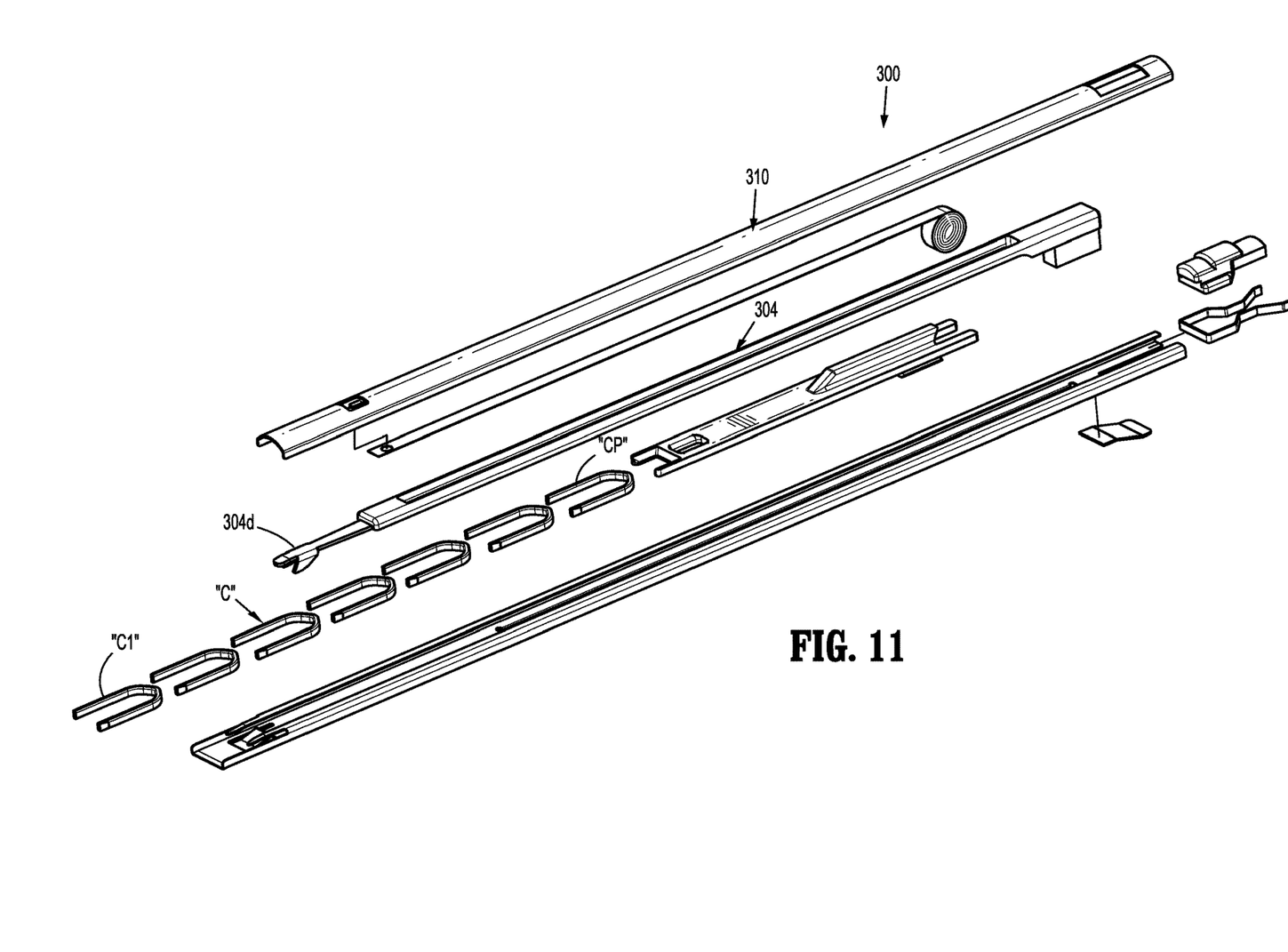
FIG. 11 is an exploded perspective view of a clip cartridge assembly of FIG. 1.

With reference now to FIG. 11, clip cartridge assembly 300 is configured for selective loading into channel 212c (FIG. 10) formed in distal end portion 212b of outer tube 212 of endoscopic assembly 200. Clip cartridge assembly 300 is loaded with a stack of surgical clips "C", e.g., 10, surgical clips "C". However, it is contemplated that clip cartridge assembly 300 may be loaded with any number of surgical clips "C". It is also contemplated that at least a final surgical clip "CP" of the stack of surgical clips "C" may be color coded to indicate to the user when final surgical clip "CP" of clip cartridge assembly 300 is loaded into jaw member 214.

For a detailed discussion of exemplary elongate shaft 210 and clip cartridge assembly 300, reference may be made to commonly-assigned U.S. Pat. Nos. 5,084,057 and 5,100,420 to Green et al., the entire contents of each of which is incorporated herein by reference. Another multiple endoscopic clip applier is disclosed in commonly-assigned U.S. Pat. No. 5,607,436 to Pratt et al., the entire contents of which is incorporated herein by reference.

An exemplary mode of operation of clip applier 10 is now described with reference to FIGS. 1-13. Prior to use, endoscopic assembly 200 (FIG. 1) is connected to handle assembly 100, and clip cartridge assembly 300 is loaded in endoscopic assembly 200. With trigger 104 of handle assembly 100 in an unactuated condition, jaw pusher tube 130 and clip pusher shaft 140 of handle assembly 100 are in an unactuated or proximal-most position. At this time, tooth 132c of release lever 132 extends across and into engagement with proximal end 140a of clip pusher shaft 140.

Figure 12:
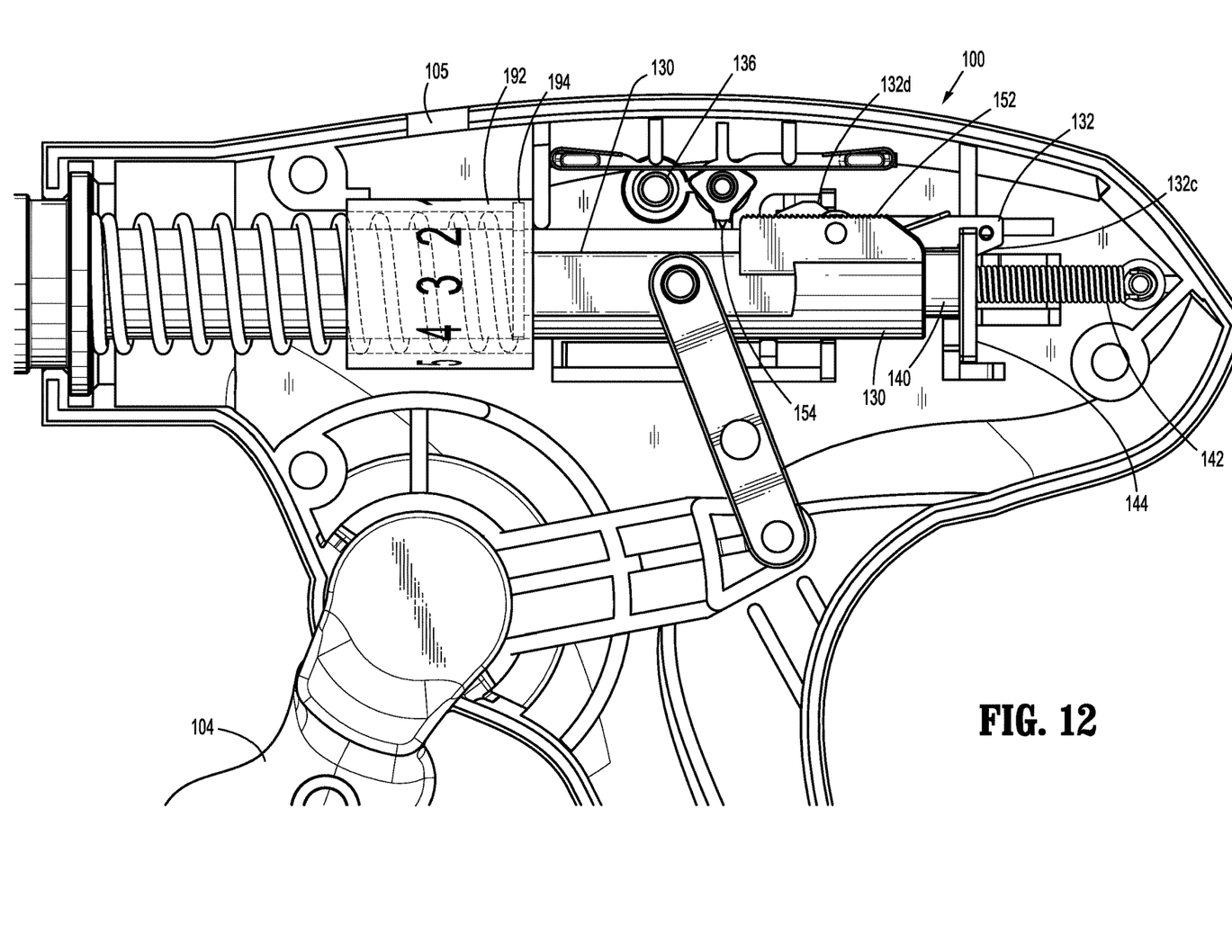
FIG. 12 is a side cross-sectional view of the handle assembly of FIG. 1 illustrating the handle assembly in an unactuated condition.

With reference to FIG. 12, as trigger 104 of handle assembly 100 is initially actuated, jaw pusher tube 130 and clip pusher shaft 140 advance distally. At this time, camming pin 194 on flange 130e of jaw pusher tube 130 slides along proximal portion $196a_1$ (FIG. 7) of continuous groove 196. Distal movement of clip pusher shaft 140 advances clip pusher bar 218 (FIG. 10) of endoscopic assembly 200 in a distal direction which, in turn, moves cartridge clip pusher bar 304 (FIG. 11) of clip cartridge assembly 300 in a distal direction to load distal-most surgical clip "$C_1$" (FIG. 11) into jaw member 214 (FIG. 10). As jaw pusher tube 130 is advanced in the distal direction, jaw closure bar 216 (FIG. 10) is advanced distally causing jaw member 214 to open, while distal-most surgical clip "$C_1$" is loaded into jaw member 214.

With particular reference to FIG. 13, as trigger 104 is further actuated, pawl 154 of ratchet assembly 150 engages teeth 152a of rack 152. Once pawl 154 engages rack 152, trigger 104 is inhibited from returning to a fully unactuated position until trigger 104 is fully actuated or until pawl 154 clears a proximal end of rack 152. At this time, camming pin 194 of firing counter assembly 190 slides to distal portion $196c_1$ (FIG. 7) through transition portion $196b_2$ (FIG. 7) and rotatable sleeve 192 begins to rotate.

As jaw pusher tube 130 is further advanced distally, jaw pusher tube 130 approaches camming pin 136. Meanwhile, clip pusher shaft 140 continues to move clip pusher bar 218 (FIG. 10) of endoscopic assembly 200 in a distal direction, which moves cartridge clip pusher bar 304 (FIG. 11) in a distal direction to complete loading of distal-most surgical clip "$C_1$" (FIG. 11) into jaw member 214.

As jaw pusher tube 130 is further advanced distally, ramp 132d of release lever 132 engages pin 136 and is pushed toward jaw pusher tube 130, while moving proximal end 132a of release lever away from jaw pusher tube 130, and thereby releasing tooth 132c of release lever 132 from proximal end 140a of clip pusher shaft 140. When tooth 132c of release lever 132 disengages clip pusher shaft 140, biasing member 142 pulls clip pusher shaft 140 proximally into abutment with stop block 144.

As clip pusher shaft 140 moves in a proximal direction, clip pusher bar 218 is moved proximally which, in turn, moves cartridge clip pusher bar 304 (FIG. 11) proximally. As cartridge clip pusher bar 304 is moved in a proximal direction, pusher 304d of cartridge clip pusher bar 304 is withdrawn from jaw member 214 and placed proximal of the next distal-most surgical clip of the stack of surgical clips "C".

As trigger 104 is fully actuated, trigger 104 continues to advance jaw pusher tube 130 of handle assembly 100 distally. Jaw pusher tube 130 acts on jaw closure bar 216 to move jaw closure bar 216 in a distal direction which, in turn, approximates jaw member 214 (FIG. 10) and forms the distal-most surgical clip "$C_1$" (FIG. 11) that has been loaded therein. At this time, pawl 154 of ratchet assembly 150 disengages rack 152 on jaw pusher tube 130. Once rack 152 clears pawl 154, trigger 104 is returned to the unactuated condition upon release thereof. As trigger 104 is returned to the unactuated condition, jaw pusher tube 130 is moved in a proximal direction until tooth 132c of release lever 132 re-engages proximal end 140a of clip pusher shaft 140. As jaw pusher tube 130 moves in a proximal direction, camming pin 194 slides into proximal portion 196a2 through transition portion 196b2 (FIG. 7) and rotates rotatable sleeve 192 a predetermined amount such that the indicia corresponding to the number of remaining surgical clips "C" is seen through window 105.

As jaw pusher tube 130 is moved in the proximal direction, jaw closure bar 216 is moved in a proximal direction causing jaw member 214 to return to the open condition. Clip applier 10 is now reset for firing of another surgical clip "C". This process may be repeated until the last surgical clip "CP" (FIG. 11) has been fired. When the last clip surgical "CP" has been fired, camming pin 194 is received in distal portion $196c_n$ (FIG. 9) to lock drive assembly 150 and firing counter assembly 190 and inhibit further actuation of trigger 104.

It is contemplated that handle assembly 100 and endoscopic assembly 200 may be sterilizable and, thus, reusable for multiple surgical procedures. It is also contemplated that clip cartridge assembly 300 may be disposable for a single use.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical device including a number of surgical clips, comprising:
   a handle assembly including:
      a housing defining a window;
      a trigger; and
      a drive member axially movable within the housing, the drive member operatively coupled with the trigger; and
   a firing counter assembly including:
      a sleeve rotatably supported about the drive member, the sleeve having a number of indicia circumferentially arranged about the sleeve, the number of indicia corresponding to the number of surgical clips in the surgical device, the sleeve defining a continuous groove; and
      a camming pin supported on the drive member for concomitant axial displacement with the drive member, the camming pin configured to slide through the continuous groove of the sleeve, wherein actuation of the trigger causes rotation of the sleeve such that the indicia corresponding to the number of surgical clips remaining in the surgical device is shown through the window of the housing.

2. The surgical device according to claim 1, wherein the continuous groove includes a plurality of proximal portions, a plurality of transition portions, and a first distal portion.

3. The surgical device according to claim 2, wherein axial movement of the drive member from a proximal-most position to a distal-most position causes the camming pin to slide from a first proximal portion of the plurality of proximal portions of the continuous groove to the first distal portion through a first transition portion of the plurality of transition portions of the continuous groove.

4. The surgical device according to claim 3, wherein axial movement of the drive member from the distal-most position to the proximal-most position causes the camming pin to slide from the first distal portion of the continuous groove to a second proximal portion of the plurality of proximal portions of the continuous groove through a second transition portion of the plurality of transition portions of the continuous groove, the first distal portion disposed distal of the second proximal portion.

5. The surgical device according to claim 4, wherein movement of the camming pin through the first or second transition portion of the plurality of transition portions of the continuous groove rotates the sleeve.

6. The surgical device according to claim 2, wherein a pair of the plurality of transition portions of the continuous groove defines a bifurcated fork with the first distal portion of the continuous groove.

7. The surgical device according to claim 6, wherein a proximal end of the first distal portion of the continuous groove is aligned with one of the pair of the plurality of transition portions of the continuous groove.

8. The surgical device according to claim 7, wherein each of the plurality of transition portions of the continuous groove defines an acute angle with respect to the plurality of proximal portions of the continuous groove.

9. The surgical device according to claim 6, wherein the plurality of proximal portions of the continuous groove are substantially parallel to each other.

10. The surgical device according to claim 2, wherein the sleeve defines a passage configured to receive the drive member of the handle assembly, the passage defining a central axis, the sleeve rotatable about the central axis.

11. The surgical device according to claim 10, wherein the plurality of proximal portions of the continuous groove are substantially parallel to the central axis.

12. The surgical device according to claim 10, wherein the first distal portion of the continuous groove is substantially parallel to the central axis of the sleeve.

13. The surgical device according to claim 10, wherein the plurality of proximal portions of the continuous groove are uniformly arranged about the central axis.

14. The surgical device according to claim 2, wherein a pair of the plurality of transition portions defines a bifurcated fork with one of the plurality of proximal portions.

15. The surgical device according to claim 2, wherein the continuous groove further includes a second distal portion, the second distal portion having a length shorter than a length of the first distal portion, the second distal portion being dimensioned to inhibit return of the drive member to a proximal-most position.

16. A surgical clip applier comprising:
   a handle assembly including:
      a housing defining a window;
      a trigger extending from the housing; and
      a drive assembly including a drive member axially movable within the housing and operatively coupled with the trigger;
   an elongate member extending distally from the handle assembly; and
   a clip cartridge assembly selectively loadable in the elongate member, the clip cartridge assembly having a number of surgical clips; and
   a firing counter assembly including:
      a sleeve rotatably supported on the drive member, the sleeve including a number of indicia corresponding to the number of surgical clips in the clip cartridge assembly, the sleeve defining a camming groove; and
      a camming pin supported on the drive member, the camming pin configured to slide through the camming groove of the sleeve, wherein actuation of the trigger causes rotation of the sleeve such that the indicia corresponding to the number of surgical clips remaining in the clip cartridge assembly is shown through the window of the housing.

17. The surgical clip applier according to claim 16, wherein movement of the camming pin through the first or second transition portion of the plurality of transition portions of the continuous groove rotates the sleeve.

18. The surgical clip applier according to claim 16, wherein the camming groove includes a plurality of proximal portions, a plurality of transition portions, and a first distal portion.

19. The surgical clip applier according to claim 18, wherein a pair of the plurality of transition portions defines a bifurcated fork with the first distal portion.

20. The surgical clip applier according to claim 18, wherein a pair of the plurality of transition portions defines a bifurcated fork with one proximal portion of the plurality of proximal portions of the camming groove.

21. The surgical clip applier according to claim 20, wherein axial movement of the drive member from a proximal-most position to a distal-most position causes the camming pin to travel from a first proximal portion of the plurality of proximal portions of the camming groove to the first distal portion through a first transition portion of the plurality of transition portions of the camming groove.

22. The surgical clip applier according to claim 21, wherein axial movement of the drive member from the distal-most position to the proximal-most position causes the camming pin to slide from the first distal portion of the camming groove to a second proximal portion of the plurality of proximal portions of the camming groove through a second transition portion of the plurality of transition portions of the camming groove.

\* \* \* \* \*